(12) United States Patent
Nugent

(10) Patent No.: US 6,362,344 B1
(45) Date of Patent: Mar. 26, 2002

(54) CATALYSTS FOR ASYMMETRIC ADDITION OF ORGANOZINC REGENTS TO ALDEHYDES AND METHOD FOR PREPARATION

(75) Inventor: William A. Nugent, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/669,386

(22) Filed: Sep. 26, 2000

Related U.S. Application Data

(62) Division of application No. 09/523,046, filed on Mar. 10, 2000, now Pat. No. 6,187,918.
(60) Provisional application No. 60/124,208, filed on Mar. 15, 1999, and provisional application No. 60/099,970, filed on Sep. 11, 1998.

(51) Int. Cl.[7] .............................................. C07D 333/24
(52) U.S. Cl. ......................... 549/79; 560/238; 568/814
(58) Field of Search ........................ 549/79; 560/238; 568/814

(56) References Cited

PUBLICATIONS

Chem. Rev. (1992) vol. 92, pp 833–856, "Enantioselective Addition of Organozinc Reagents to Aldehydes", Kenso Soai and Seiji Niwa.

Angew. Chem. Int. Ed. Engl., 30 (1991) pp 49–69, "Enantioselective Addition of Organometallic Reagents to Carbonyl Compounds: Chirality Transfer, Multiplication, and Amplification", Ryoji Noyori asnd Masato Kitamura.

J. Am. Chem. Soc. (1991) vol. 113, pp 3893–3904, "Oxidative Photofragmentation of a,b–Amino Alchols via Single Electron Transfer: Cooperative Reactivity of Donor and Acceptor Ion Radicals in Photogenerated Contact Radical Ion Pairs", Xiaohong Ci, Matthew A. Kellett, and David G. Whitten.

J. Org. Chem. (1991), vol. 56, pp 4264–4268, "Chiral N,N–Dialkylnorephedrines as Catalysts of the Highly Enantioselective Addition of Dialkylzines to Aliphatic and Aromatic Aldehydes. The Asymmetric Synthesis of Secondary Aliphatic and Aromatic Alcohols of High Optical Purity", Kenso Soai, Shuji Yokoyama, and Tomoiki Hayaasaka.

J. Am. Chem. Soc. (1986) vol. 108, pp 6071–6072, "Catalytic Asymmetric Induction. Highly Enantioselective Addition of Dialkyzines to Aldehydes", M. Kitamura, S. Suga, K. Kawai, and R. Noyori.

*Primary Examiner*—Robert W. Ramsuer
(74) *Attorney, Agent, or Firm*—Kenneth B. Rubin; Peter L. Dolan

(57) ABSTRACT

Chiral aminoalcohol catalysts and methods for their preparation are provided. The first catalyst is prepared via selective hydrogenation of one of two benzene rings in a precursor. The aminoalcohol promotes the asymmetric addition of organozinc reagents to aldehydes to afford optically active alcohols or their esters. The second catalyst is prepared by selective dialkylation of 3-exo-aminoisoborneol with a 2-haloethyl ether. The aminoalcohol promotes the addition of organozinc reagents to aliphatic aldehydes containing a β-branch with greatly enhanced enantioselectivity relative to DAIB.

6 Claims, No Drawings

CATALYSTS FOR ASYMMETRIC ADDITION OF ORGANOZINC REGENTS TO ALDEHYDES AND METHOD FOR PREPARATION

This application is a division of U.S. application Ser. No. 09/523,046 filed Mar. 10, 2000, now U.S. Pat. No. 6,187,918, which claims the benefit of U.S. Provisional Application No. 60/0124,208 filed Mar. 15, 1999 and which claims the benefit of U.S. Provisional Application No. 60/099,970, filed Sep. 11, 1998.

FIELD OF INVENTION

The invention generally relates to novel chiral aminoalcohol catalysts. The first is prepared by selectively hydrogenating one of two benzene rings in a precursor. The second is by selective dialkylation of a 3-exo-aminoisoborneol with a 2-haloethyl ether. In both cases, the aminoalcohol promotes the asymmetric addition of organozinc reagents to aldehydes to yield optically active alcohols or their esters.

BACKGROUND OF THE INVENTION

Modem organic chemists have as one goal the development of new synthetic routes for the controlled, efficient production of asymmetric compounds. Saturated carbon atoms, constituting the backbones of most organic compounds, are attached to adjacent atoms through a tetrahedral arrangement of chemical bonds. If the four bonds are to different atoms or groups, the central carbon provides a chiral, or asymmetric, center and the compound therefore may have the ability to exist in two mirror image, or enantiomeric, forms. It is crucial when synthetic organic chemists attempt to prepare these asymmetric compounds to have a means to produce the desired enantiomer because compounds of the wrong enantiomeric form often lack desirable biological, physical or chemical properties.

A particularly attractive approach to the synthesis of optically active compounds is the catalytic asymmetric generation of carbon-carbon bonds. This approach is highly efficient because the optical activity is installed during the assembly of the carbon skeleton rather than as a separate, subsequent operation. Among such reactions the enantioselective addition of organometallic reagents to aldehydes has received much attention in the literature. This transformation represents the enantioselective version of the venerable Grignard addition and affords broadly useful, optically active secondary alcohols as products. Organozinc reagents are usually employed as the organometallic reactant since they do not react with aldehydes in the absence of a catalyst.

General reviews cite the use of optically active β-aminoalcohols to catalyze the asymmetric addition of organozinc reagents to aldehydes (Noyori, R., Kitamura, M., Angew. Chem., Int. Ed. Engl. 1991, 30, 49; Soai, K.; Niwa, S. Chem. Rev. 1992, 92, 833). Among such catalysts, the best known and most widely used appears to be 3-exo-(dimethylamino)isoborneol, more commonly known as DAIB (Kitamura, M. et al., J. Am. Chem. Soc. 1986, 108, 6071). DAIB allows highly selective addition of organozinc reagents to certain aldehydes, especially aryl derivatives. However, DAIB requires an expensive and complex 6-step synthesis and is not suitable for addition of organozinc reagents to sterically encumbered aldehydes such as pivalaldehyde. Other aminoalcohols such as N,N-dibutylnorephedrine or DBNE (Soai, K. et al., J. Org. Chem. 1991, 56, 4264) are easier to prepare but are less selective catalysts than DAIB.

Clearly, a need exists for an improved catalyst for the asymmetric addition of organozinc reagents to aldehydes which is both readily synthesized and provides high selectivity with a wide range of aldehyde substrates. The present invention provides an improved process for the synthesis of compounds in a desired enantiomeric form. Other objects and advantages of the invention will become apparent to those skilled in the art upon reference to the detailed description, which hereinafter follows.

SUMMARY OF THE INVENTION

The present invention provides for an erythro-β-aminoalcohol compound of Formula 1. The compound is preferably optically active.

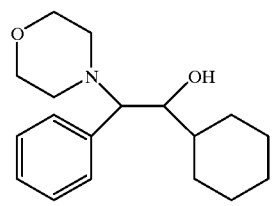

1

The invention also provides for a process to prepare an erythro-β-aminoalcohol compound of Formula 1 comprising selectively hydrogenating an erythro-β-aminoalcohol of Formula 2 to form the erythro-β-aminoalcohol of Formula 1.

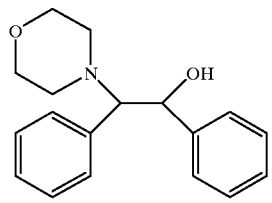

2

The hydrogenation is preferably performed in the presence of a catalyst comprising rhodium supported on an inorganic support. More preferably, the catalyst is 5% rhodium on alumina. A preferred form of the process is where the erythro-β-aminoalcohol compound of Formula 1 is optically active. Also preferred is where β-aminoalcohol of Formula 2 is prepared by reacting stilbene oxide with morpholine.

Another aspect of the invention provides for a process to prepare a compound of the Formula 6:

6 comprising: a) contacting an aldehyde of formula RC(O)H with a zinc compound of formula R'ZnR" in the presence of a catalytic amount of an erythro-β-amino-alcohol of Formula 1; b) further contacting the reactants with $Y_2O$ to form the corresponding ester or alcohol of Formula 6 wherein R, R', and R" are hydrocarbyl or substituted hydrocarbyl; Y is a hydrogen or alkanoyl group; and $Y_2O$ is a carboxylic acid anhydride or water.

A preferred process is where the erythro-β-aminoalcohol and the compound of Formula 6 are optically active. More preferred is where the compound of Formula 6 has an enantiomeric excess of greater than about 80%, and most preferred is where the compound of Formula 6 has a high level of enantiomeric purity.

Another preferred process is where Y is hydrogen or acetyl. More preferred is where R is selected from the group consisting of phenyl, n-hexyl, 3-thienyl, cyclohexyl, 1,1-dimethyl-3-butenyl, isopropyl, 1-butenyl and isobutyl; and R' is selected from the group consisting of ethyl, methyl and 5-chloropentenyl.

DETAILED DESCRIPTION OF THE PREFERRED EMBODIMENTS

The present invention consists of a morpholine-substituted erythro-β-aminoalcohol compound comprising one of the compounds of Formula 1

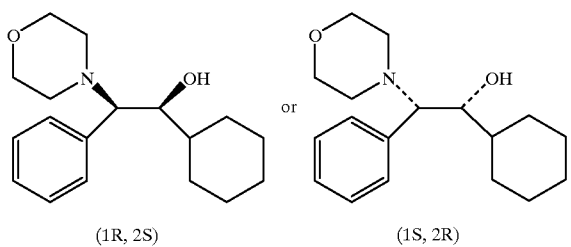

(1R, 2S)      (1S, 2R)

and a process for their preparation.

The following definitions are used herein:

The term "alkanoyl" means a monovalent radical of the formula —C(O)R", where R" is hydrogen, hydrocarbyl or substituted hydrocarbyl group.

The term "carboxylic acid anhydride" means a compound containing the grouping —C(O)O(O)C—, wherein the free valencies are to other carbon atoms.

The term "chiral" means "existing as a pair of enantiomers". These stereoisomers, designated the R and S enantiomers, are mirror images of one another. A chiral material may either contain an equal amount of the R and S isomers (in which case it is called "racemic") or it may contain inequivalent amounts of R and S isomer (in which case it is called "optically active"). The extent of this inequivalence is measured as the "enantiomeric excess".

When two chiral centers exist in one molecule, there can be up to four different stereoisomers. In such a molecule, if the two centers have one substituent in common, they can be further characterized as "erythro" or "threo". When the two identical substituents are on the same side when drawn in the standard Fischer convention, the molecule is labeled erythro. (For a further discussion, see *Advanced Organic Chemistry*, 2$^{nd}$ edition, J. March, Ed., 1977, pp 104–106.)

The term "enantiomeric excess" means the difference between the percent of R enantiomer and the percent of S enantiomer of an optically active compound. For example, a compound that contains 75% S isomer and 25% R isomer will have an enantiomeric excess of 50%.

The term "high level of enantiomeric purity" means having an enantiomeric excess of greater than or equal to about 90%, preferably greater than or equal to about 95%.

The term "enantioselective" means having the ability to produce a product in an optically active form.

By the term "hydrocarbyl" Applicant includes all alkyl, aryl, aralkyl or alkylaryl carbon substituents, either straight chain, branched or cyclic. "Substituted hydrocarbyl" means a hydrocarbyl group containing a substituent such as, but not limited to, halide or oxygen functionalities such as, but not limited to, ether, ester, and acetal.

A preferred form of the invention is a morpholine-substituted β-amino-alcohol compound that is optically active.

Applicant has further discovered that the aminoalcohol of Formula 1 is an enantioselective catalyst for the addition of organozinc reagents to many aldehydes, including sterically hindered aldehydes, to produce optically active secondary alcohols or their ester derivatives. Optically active alcohols and esters are important intermediates for the manufacture of many biologically active compounds. One such reaction is the preparation of enantiopure succinate derivatives, which are components of matrix metalloproteinase inhibitors.

Another aspect of the invention is a process for the preparation of the morpholine-substituted erythro-β-aminoalcohol of Formula 1 comprising selectively hydrogenating the morpholine-substituted erythro-β-aminoalcohol of Formula 2 to form the morpholine-substituted β-aminoalcohol of Formula 1 in the presence of a catalytic amount of Rh supported on a inorganic support.

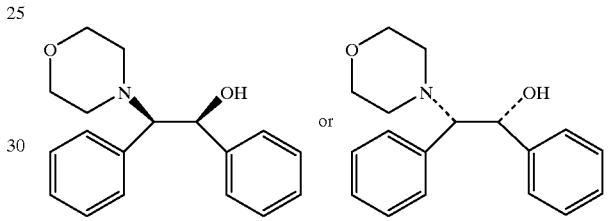

A preferred aspect of this invention is a process to prepare the morpholine-substituted erythro-β-aminoalcohol of Formula 1 in an optically active form. Either the (1R, 2S) or (1S, 2R) enantiomer of Formula 1 can be prepared, depending on which enantiomer of 2 is used as starting material.

Any procedure known in the art can be used to prepare the morpholine-substituted erythro-β-aminoalcohol of Formula 2 that is used as the starting material. One such procedure uses stilbene oxide as a precursor and comprises reacting (R, R)- or (S, S)-stilbene oxide with morpholine to prepare the corresponding (1R, 2S)- or (1S, 2R)-morpholine-substituted β-aminoalcohol of Formula 2, at a temperature of 50° C. to 200° C., either in an inert solvent with suitable boiling point or, preferably, in the absence of solvent. Another procedure is described in Xi, C. et al., *J. Am. Chem. Soc.* 1991, 113, 3893.

A preferred aspect of this invention is a process to prepare the morpholine-substituted β-aminoalcohol of Formula 2 in an optically active form. This is done by using an optically active form of stilbene oxide as a starting material.

The hydrogenation is performed in the presence of a catalyst that consists of rhodium supported on an inorganic support. Suitable supports include, but are not limited to alumina, silica and titania, and the loading of rhodium can be from 0.5% to 20%. Most preferably, the catalyst is 5% rhodium on alumina.

The hydrogen pressure can be about 10 to 1000 atmospheres (1 to 100 MPa) with about 50 to 200 atmospheres (5 to 20 MPa) most preferred.

The hydrogenation reaction is carried out in a protic solvent, preferably an alcohol. Suitable solvents include, but are not limited to methanol, ethanol, isopropanol, n-propanol, or t-butyl alcohol.

In order to provide the necessary acidic environment, an acidic additive is present in a molar amount greater than the amount of aminoalcohol 2 in the system. Examples of acidic additives include, but are not limited to, hydrochloric acid, phosphoric acid, formic acid, propionic acid, or acetic acid. Organic carboxylic acids are preferred and acetic acid is most preferred.

The hydrogenation is carried out between 0° C. and 200° C., preferably between 25° C. and 100° C.

The invention further includes a method for the preparation of alcohol or esters using 1 as a catalyst. The general scheme can be pictured as follows:

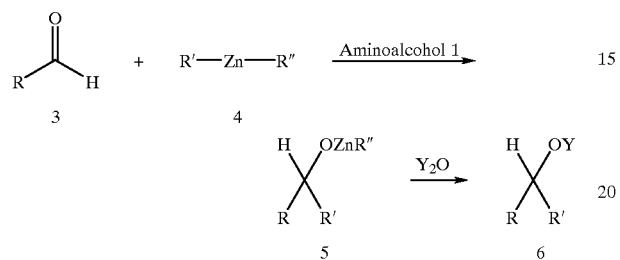

The reaction comprises: a) contacting an aldehyde of formula RC(O)H with a zinc compound of formula R'ZnR" in the presence of a catalytic amount of an aminoalcohol of Formula 1; b) further contacting the reactants with $Y_2O$ to form the corresponding ester or alcohol of Formula 6; wherein R, R', and R" are hydrocarbyl or substituted hydrocarbyl; Y is hydrogen or a alkanoyl group; and $Y_2O$ is a carboxylic acid anhydride or water.

Preferred processes are where the aminoalcohol 1 and the compound of Formula 6 are optically active. The catalyst enantiomer chosen determines which enantiomer of the product is prepared. More preferred is where the compound of Formula 6 has an enantiomeric excess of greater than about 80%. Most preferred is where the compound of Formula 6 has a high level of enantiomeric purity.

Also preferred is where Y is hydrogen or acetyl and where R is selected from the group consisting of phenyl, n-hexyl, 3-thienyl, cyclohexyl, 1,1-dimethyl-3-butenyl, isopropyl, cyclopropyl, 1-butenyl, and isobutyl, and R' is selected from the group consisting of ethyl, methyl, and 5-chloropentenyl.

The reaction is carried out in a solvent which is aprotic and, preferably, apolar, and which is inert to all reagents and products. Examples of suitable solvents include, but are not limited to, carbon tetrachloride, 1,2-dichloroethane, pentane, hexane, heptane, cyclohexane, benzene, toluene, or mixtures thereof.

The amount of organozinc reagent used relative to aldehyde substrate can be between 1 and 5 molar equivalents, and, preferably about 2 molar equivalents;

The amount of aminoalcohol 1 used as catalyst relative to aldehyde substrate can be between 0.5% and 20%, and, preferably between 2% and 10%.

The temperature can between −25° C. and 50° C., preferably at between 0° C. and 25° C. It is, however, most convenient to carry out the reaction at ambient temperature and pressure.

The optically active zinc alkoxide 5 formed in the above reaction may simply be treated with water to release the optically active alcohol 6, Y=H. Alternatively, in certain cases it may be desirable to treat the reaction mixture with one molar equivalent of acetic anhydride to directly convert the product to the corresponding acetate ester 6, Y=acetyl. Both procedures are conveniently carried out at room temperature.

Applicant has also discovered a second aminoalcohol composition A which promotes the addition of organozinc reagents to aldehydes in a highly enantio-selective manner. Aminoalcohol A is prepared by selective dialkylation of 3-exo-aminoisoborneol B with a 2-haloethyl ether. Either enantiomer of A can be prepared, depending on which enantiomer of B is used as starting material. Aminoalcohol A shares a common camphor backbone structure with the known aminoalcohol catalyst DAIB but it differs from DAIB in several unobvious aspects. Thus, DAIB is an air-sensitive liquid which is prepared from B in three steps; in contrast A is an air-stable crystalline solid which is prepared from B in a single step. In addition, A unexpectedly promotes the addition of organozinc reagents to aliphatic aldehydes containing a β-branch (i.e., isobutyraldehyde, cyclohexanecarboxaldehyde) with greatly enhanced enantioselectivity as compared with DAIB.

A general reaction for the preparation of A can be described as follows:

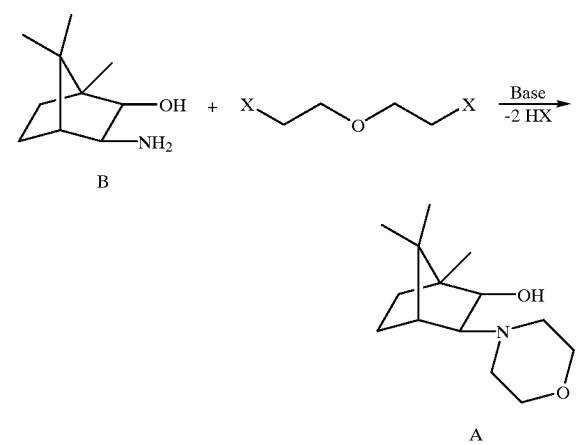

where
the halide substituent X in the 2-haloethyl ether is chloride, bromide, or iodide; preferably the 2-haloether is 2-bromoethyl ether; the base is a mild organic or inorganic which is compatible with both the primary amine and the halide functional groups and whose basicity is sufficient to deprotonate the unreactive conjugate acid of B when it is protonated by HX. Examples of useful bases include triethylamine, diisopropylethylamine, sodium carbonate and sodium bicarbonate; the solvent is a protic or aprotic organic liquid which is compatible with both the primary amine and haloethyl functional groups and is readily separable from A either by distillation or differential solubility in water. Examples of suitable solvents are dimethylsulfoxide, dimethyl formamide, chlorobenzene, and toluene. Alternatively, the reaction may be run in a two phase system consisting of water and an immiscible organic solvent such as toluene, and optionally in the presence of a phase transfer catalyst; the reaction temperature is between 0° C. and 100° C. For convenience, the reaction is preferably carried out at room temperature and at atmospheric pressure.

The products of the invention can easily be converted to chiral intermediates useful in the manufacture of pharmaceuticals. Optically-active secondary alcohols 6 can be converted to the ether, ester, carbamate, silyl ether or arenesulfonate functionality without loss of optical activity by methods well known in the art. Moreover, the arenesulfonate derivatives of such secondary alcohols undergo nucleophilic displacement reactions with, for example, azide, cyanide, or thiolate to afford optically active products with inversion of stereochemistry. The optically active ester forms of Formula 6, especially the acetate esters, can be hydrolyzed under either basic or acid conditions to the optically active alcohols.

Although the Applicant contemplates many possible uses for the products of the instant invention, one possible example is use as an intermediate for metalloproteinase inhibitor.

MATERIALS AND METHODS (R,R)-Stilbene oxide and (S,S)-stilbene oxide were prepared using a standard literature procedure (Chang, H.-T., Sharpless, K. B. *J. Org. Chem.* 1996, 61, 6456). Diethylzinc and dimethylzinc solutions, aldehyde substrates, and all other organic starting materials were purchased from Aldrich Chemical Company, Milwaukee, Wis. The enolizable aldehydes cyclohexanecarboxaldehyde, isobutyraldehyde, and hexanal were distilled immediately prior to use. The Cyclodex B™ capillary GC column used to determine enantiomeric excess was purchased from J&W Scientific, Folsom, Calif.

EXAMPLES

The following non-limiting examples are intended to further illustrate the invention.

EXAMPLE 1

Aminoalcohol 2 was prepared as follows. A vial containing morpholine (0.96 g, 11 mmol) and (R,R)-stilbene oxide (2.34 g, 12 mmol) was heated in a 90° C. oil bath for 1 week. The crude reaction product was crystallized from hot toluene (20 mL) to afford (1R,2S)-1,2-diphenyl-2-(N-morpholino) ethanol (aminoalcohol 2, 2.24 g, 72%) as a white crystalline solid m.p. 132–134° C. $[\alpha]_D^{25}$=−64.3, c=1.05 g/100 mL DMSO. Anal. for $C_{18}H_{21}NO_2$. Calcd: C, 76.29; H, 7.47; N, 4.94; found: C, 76.11; H, 7.35; N, 4.98. $^1$H NMR (CDCl$_3$/ TMS): δ 2.53 (m, 2 H), 2.65 (br s, 2 H), 3.26 (br s, 1 H), 3.36 (d, 1 H), 3.72 (m, 4 H), 5.33 (d, 1 H), 6.92–7.01 (m, 4 H), 7.05–7.17 (m, 6 H). $^{13}$C NMR (CDCl$_3$/TMS): δ 52.02, 67.16, 71.26, 76.50, 126.16, 126.90, 127.44, 127.60, 127.64, 129.59, 135.61, 140.83.

Aminoalcohol 2 (2.24 g, 7.90 mmol) was dissolved in methanol (100 mL) and acetic acid (4 mmol). The solution was hydrogenated over 5% rhodium on alumina catalyst (1.00 g) at 1500 psi (10.3 MPa) and 50° C. for 16 h. The reaction mixture was filtered and the solvent was distilled at reduced pressure. The residue was stirred with 1N sodium hydroxide (50 mL) and ether (100 mL). The ether layer was separated and the aqueous layer was further extracted with ether (3×50 mL). After distillation of the solvent, the residue from the combined ether layer was crystallized from hot heptane to afford (1R,2S)-1-cyclohexyl-2-phenyl-2-(N-morpholino)ethanol (aminoalcohol 1, 1.62 g, 71%) as a white crystalline solid, m.p. 110–111° C., $[\alpha]_D^{25}$=+13.6, c=2.01 g/100 mL ethanol. Selective hydrogenation of the benzene ring adjacent to the hydroxyl group was confirmed by means of an x-ray crystal structure, which also confirmed that the compound was essentially 100% ee. Anal. for $C_{18}H_{27}NO_2$. Calcd: C, 74.70; H, 9.40, N, 4.84; found: C, 74.61; H, 9.25; N, 4.90. $^1$H NMR (CDCl$_3$/TMS): δ 0.82–1.14 (m, 6 H), 1.53–1.71 (m, 4 H), 2.00 (m, 1 H), 2.29 (m, 2 H), 2.54 (br s, 2 H), 3.24 (m, 1 H), 3.30 (m, 1 H), 3.30 (br s, 1 H), 3.48 (M, 4 H), 3.78 (m, 1 H), 6.92–7.51 (m, 5 H). $^{13}$C NMR (CDCl$_3$/TMS): δ 25.59, 25.67, 26.52, 28.49, 29.41, 39.73, 52.00. 67.24, 72.09, 72.97, 127.70, 128.18, 129.92, 136.70.

EXAMPLE 2

To a vial containing aminoalcohol 1 (0.05 g, 0.17 mmol) prepared as in Example 1 was added a solution containing benzaldehyde (0.32 g, 3.0 mmol), toluene (3.0 mL), and 1 M diethylzinc in hexane (6.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ethyl acetate as eluant. The product (+)-1-phenylpropyl acetate (0.46 g, 86%) was isolated as a colorless liquid by distillation of the solvent at reduced pressure. Anal. for $C_{11}H_{14}O_2$. Calcd: C, 74.13; H, 7.92; found: C, 74.32; H, 7.82. $^1$H NMR (CDCl$_3$/TMS): δ 0.87 (t, 3 H, J=7), 1.79, (m, 1 H), 1.90 (m, 1 H), 2.06 (s, 3 H), 5.66 (t, 1 H, J=7), 7.1–7.7 (m, 5 H). $^{13}$C NMR (CDCl$_3$/ TMS): δ 9.89, 21.23, 29.30, 77.66, 126.76, 128.81, 128.57, 140.58, 170.36. $[\alpha]_D^{25}$=+103.4, c=2.15 g/100 mL chloroform. Chiral capillary gas chromatographic analysis at 120° C. on Cyclodex B stationary phase (J & W Scientific) indicated that the enantiomeric excess of the product was 98%.

EXAMPLE 3

To a vial containing aminoalcohol 1 (0.05 g, 0.17 mmol) prepared as in Example 1 was added a solution containing freshly distilled hexanal (0.30 g, 3.0 mmol), toluene (3.0 mL), and 1 M diethylzinc in hexane (6.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 95% hexane and 5% ethyl acetate as eluant. The product (+)-3-octyl acetate (0.34 g, 66%) was isolated as a colorless liquid by distillation of the solvent at reduced pressure. Anal. for $C_{10}H_{20}O_2$. Calcd: C, 69.72; H, 11.70; found: C, 70.08; H, 11.86. $^1$H NMR (CDCl$_3$/TMS): δ 0.86 (t, 6 H, J=7), 1.22–1.33 (br m, 6 H), 1.45–1.60 (m, 4 H), 2.03 (s, 3 H), 4.80 (m, 1 H). $^{13}$C NMR (CDCl$_3$/TMS): δ 9.58, 14.00, 21.25, 22.57, 25.02, 26.98, 31.62, 33.60, 75.57, 170.97. $[\alpha]_D^{25}$=+7.0, c=2.01 g/100 mL chloroform. Chiral capillary gas chromatographic analysis at 100° C. on Cyclodex B stationary phase (J & W Scientific) indicated that the enantiomeric excess of the product was 86%.

EXAMPLE 4

To a roundbottom flask containing aminoalcohol 1 (0.05 g, 0.17 mmol) prepared as in Example 1 and 1 M diethylzinc in hexane (6.0 mL) was added dropwise a solution of 3-thiophenecarboxaldehyde (0.32 g, 3.0 mmol) in toluene (3.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ethyl acetate as eluant. The product (+)-1-(3-thienyl)propyl acetate (0.45 g, 81%) was isolated as a colorless liquid by distillation at reduced pressure. Anal. for $C_9H_{12}O_2S$. Calcd: C, 58.67; H, 6.56; found: C, 58.80; H, 6.75. $^1H$ NMR (CDCl$_3$/TMS): δ 1.86 (t, 3 H, J=7), 1.80–1.88 (m, 1 H), 1.88–1.97 (m, 1 H), 2.04 (s, 3 H), 5.81 (t, 1 H, J=7), 7.05 (m 1 H), 7.20 (m, 1 H), 7.26 (m, 1 H). $^{13}C$ NMR (CDCl$_3$/TMS): δ 9.85, 21.22, 28.58, 73.10, 122.34, 125.87, 126.04, 141.46, 170.39. $[α]_D^{25}$=+131.7, c=2.06 g/100 mL chloroform. Chiral capillary gas chromatographic analysis at 120° C. on Cyclodex B stationary phase (J & W Scientific) indicated that the enantiomeric excess of the product was 96%.

EXAMPLE 5

To a vial containing aminoalcohol 1 (0.05 g, 0.17 mmol) prepared as in Example 1 was added a solution containing freshly distilled cyclohexane-carboxaldehyde (0.34 g, 3.0 mmol), toluene (3.0 mL), and 1 M diethylzinc in hexane (6.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ethyl acetate as eluant. The product (+)-1-cyclohexylpropyl acetate (0.45 g, 81%) was isolated as a colorless liquid by distillation at reduced pressure. Anal. for $C_{11}H_{20}O_2$. Calcd: C, 71.70; H, 10.94; found: C, 71.41; H, 10.69. $^1H$ NMR (CDCl$_3$/TMS): δ 0.85 (t, 3 H, J=7), 0.98 (m, 2 H), 1.08–1.26 (m, 3 H), 1.42–1.75 (m, 8 H), 2.04 (s, 3 H), 4.66 (m, 1 H). $^{13}C$ NMR (CDCl$_3$/TMS): δ 9.80, 21.14, 24.11, 26.21, 26.58, 28.22, 40.90, 79.25, 171.09. $[α]_D^{25}$=+27.6, c=2.06 g/100 mL chloroform. Chiral capillary gas chromatographic analysis at 120° C. on Cyclodex B stationary phase (J & W Scientific) indicated that the enantiomeric excess of the product was 97%.

EXAMPLE 6

To a vial containing aminoalcohol 1 (0.05 g, 0.17 mmol) prepared as in Example 1 was added a solution containing 2,2-dimethyl4-pentenal (0.34 g, 90% pure, 2.7 mmol), toluene (3.0 mL), and 1 M diethylzinc in hexane (6.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 95% hexane and 5% ether as eluant. The product (+)-3-acetoxy-4,4-dimethylhept-1-ene (0.39 g, 78%) was isolated as a colorless liquid by distilla-tion of the solvent at reduced pressure. Anal. for $C_{11}H_{20}O_2$. Calcd: C, 71.70; H, 10.94; found: C, 71.75; H, 10.66. $^1H$ NMR (CDCl$_3$/TMS): δ 0.84 (s+t, 6 H total), 0.87 (s, 3 H), 1.46 (m, 1 H), 1.62 (m, 1 H), 1.89–2.06 (m, 2 H), 2.07 (s, 3 H), 4.71 (dd, 1 H), 4.96–5.05 (m, 2 H), 5.81 (m, 1 H). $^{13}C$ NMR (CDCl$_3$/TMS): δ 10.96, 21.02, 22.33, 23.12, 37.41, 43.46, 81.41, 117.37, 134.74, 171.11. $[α]_D^{25}$=+14.2, c=2.02 g/100 mL chloroform. Chiral capillary gas chromatographic analysis at 100° C. on Cyclodex B stationary phase (J & W Scientific) indicated that the enantiomeric excess of the product was 98%.

EXAMPLE 7

A vial was charged with aminoalcohol 1 (0.0074 g, 0.026 mmol) prepared as in Example 1. To the vial was added 1.60 mL of a stock solution containing trimethylacetaldehyde (0.26 g), chlorobenzene internal standard (0.26 g), 1 M diethylzinc in hexane (6.0 mL), and toluene (3.0 mL). After 48 h, acetic anhydride (0.200 mL) was added. After an additional 72 h, a sample of the solution was analyzed by gas chromatography at 70° C. on a Cyclodex B stationary phase. The product 3-acetoxy-2,2-dimethylpentane was formed in 73% yield and 98% enantiomeric excess. The identity and yield of the product was established by comparison with an authentic sample prepared by treatment of racemic 2-methyl-3-pentanol with acetic anhydride.

In a separate experiment, the amount of catalyst was increased to 0.0146 g and the amount of stock solution was 1.58 mL. In this case the yield was 78% and the enantiomeric excess was 98%.

EXAMPLE 8

A vial was charged with aminoalcohol 1 (0.0067 g, 0.023 mmol) prepared as in Example 1. To the vial was added 1.45 mL of a stock solution containing freshly distilled isobutyraldehyde (0.22 g), chlorobenzene internal standard (0.22 g), 1 M diethylzinc in hexane (6.0 mL), and toluene (3.0 mL). After 48 h, acetic anhydride (0.200 mL) was added. After an additional 72 h, a sample of the solution was analyzed by gas chromatography at 70° C. on a Cyclodex B stationary phase. The product 3-acetoxy-2-methylpentane was formed in 100% yield and 97% enantiomeric excess. The identity and yield of the product was established by comparison with an authentic sample prepared by treatment of racemic 2,2-dimethyl-3-pentanol with acetic anhydride.

In a separate experiment, the amount of catalyst was increased to 0.0148 g and the amount of stock solution was 1.60 mL. In this case the yield was 100% and the enantiomeric excess was 98%.

EXAMPLE 9

A vial was charged with aminoalcohol 1 (0.0032 g, 0.011 mmol) prepared as in Example 1. To the vial was added 1.62 mL of a stock solution containing trans-2-pentenal (0.34 g), t-butylbenzene internal standard (0.25 g), 1 M diethylzinc in hexane (8.0 mL), and toluene (4.0 mL). After 48 h, acetic anhydride (0.200 mL) was added. After an additional 72 h, a sample of the solution was analyzed by gas chromatography at 80° C. on a Cyclodex B stationary phase. The product trans4hepten-3-yl acetate was formed 85% enantiomeric excess.

In a separate experiment, the amount of catalyst was increased to 0.0073 g and the amount of stock solution was 1.62 mL. In this case the enantiomeric excess was 86%.

EXAMPLE 10

To a vial containing aminoalcohol 1 (0.05 g, 0.17 mmol) prepared as in Example 1 was added a solution containing benzaldehyde (0.32 g, 3.0 mmol), toluene (3.0 mL), and 1 M dimethylzinc in heptane (6.0 mL). After 3 days at room temperature, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 70% hexane and 30% ethyl acetate as eluant. The solvent was distilled to afford (R)-(+)-sec-phenethyl alcohol (0.27 grams, 73%) with spectroscopic properties identical to a commercial sample. $[\alpha]_D^{25}=+55.3$, c=1.96 g/100 mL chloroform indicating enantiomeric excess was 99%.

EXAMPLE 11

A solution of 9-borabicyclononane (0.24 g, 2.0 mmol) in THF (5 mL) was added dropwise to a solution of 5-chloro-1-pentyne (0.21 g, 2.0 mmol) in THF (5 mL). After 1 h, the solvent was removed at reduced pressure. The resultant vinyl boron derivative was dissolved in toluene (5 mL) and aminoalcohol 1 (0.05 g, 0.17 mmol) prepared as in Example 1 was added. Then 1 M diethylzinc in hexane (3 mL, 3 mmol) was added via syringe at −78° C., forming ethyl-(5-chloro-1-pentenyl)zinc in situ. The dry ice bath was replaced with a wet ice bath and immediately a solution of isobutyraldehyde (0.17 g, 2.4 mmol) in hexane (5 mL) was added dropwise. After 1 hour the wet ice bath was removed and the mixture was stirred at room temperature for 8 h. Acetic anhydride (500 μL) was added and the mixture was allowed to stand overnight. GC analysis at 130° C. on Cyclodex B revealed that trans-3-acetoxy-2-methyl-8-chlorooct-4-ene had been formed in 92% enantiomeric excess.

EXAMPLE 12

To a vial containing aminoalcohol 1 (0.05 g, 0.17 mmol) prepared as in Example 1 was added a solution containing freshly distilled cyclopropane-carboxaldehyde (0.21 g, 3.0 mmol), toluene (3.0 mL), and 1 M diethylzinc in hexane (6.0 mL). After 3 days at room temperature, acetic anhydride (1.2 mL, 13 mmol) was added. After 2 additional days, the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ether as eluant. The product 1-cyclypropropyl acetate (0.34 g, 80%) was isolated as a colorless liquid by distillation at reduced pressure. Product identity was confirmed by GC and NMR comparison with an authentic sample. Chiral capillary gas chromatographic analysis at 55° C. on Cyclodex B stationary phase (J & W Scientific) was complicated by partial overlap of the enantiomers but indicated that the enantiomeric excess of the product was approximately 90%.

EXAMPLE 13

(2S)-(−)-3-exo-aminoisoborneol (aminoalcohol B) was prepared by a standard literature procedure (R. A. Chittenden and G. H. Cooper, J. Chem. Soc., C, 1970,49). Aminoalcohol B (1.37 g, 8.09 mmol) was dissolved in a mixture of dimethyl sulfoxide (10 mL) and triethylamine (2.48 g, 24.5 mmol). A solution of 2-bromoethyl ether (2.70 g, 90% pure, 10.5 mmol) in dimethyl sulfoxide (5 mL) was added dropwise and the mixture was stirred for 3 days. The mixture was added to a separatory funnel containing 75 mL water and 25 mL of 1 N sodium hydroxide. The crude aminoalcohol A was extracted into ether (3×50 mL) and the solvent was distilled at reduced pressure. The residue was extracted into 1 N HCl (15 mL) and was subsequently released by addition of 1 N sodium hydroxide (20 mL) and was extracted into 3×50 mL of ether. The solvent was again distilled at reduced pressure.

The crude A was dissolved in 30 mL of hexane, decanted from a small amount of water, and the solution was cooled to −25° C. overnight to produce (2S)-(−)-3-exo-(N-morpholino)isoborneol (0.78 g, 40%) as a white crystalline solid, m.p. 64–65° C.

Anal. for $C_{14}H_{25}NO_2$. Calcd: C, 70.25; H, 10.53; N, 5.85; found: C, 70.20; H, 11.02, N, 5.91. $^1$H NMR ($C_6H_6$/TMS): δ 0.69 (s, 3 H), 0.73 (m, 1 H), 0.88 (m, 1 H), 1.04 (s, 3 H), 1.15 9s, 3 H), 1.31 (td, 1 H), 1.52 (m, 1 H), 1.67 (d, 1 H), 1.99 (d, 1 H), 2.13 (br, 2 H), 2.31 (br, 2 H), 3.32–3.42 (m, 5 H total), 3.92 (br d, 1 H). $^{13}$C NMR ($C_6H_6$/TMS): δ 11.88, 21.10, 22.19, 27.99, 32.56, 45.35, 46.64, 49.52, 66.82, 73.37, 79.03.

EXAMPLE 14

To a flask containing aminoalcohol A (0.036 g, 0.15 mmol) prepared as in Example 13 was added benzaldehyde (0.32 g, 3.0 mmol) and toluene (3.0 mL). The flask was cooled to 0° C. and 1 M diethylzinc in hexane (6.0 mL) was added dropwise. After 3 hours at 0° C., acetic anhydride (1.2 mL, 13 mmol) was added. After 18 hours the mixture was diluted in ether (50 mL) and the reaction was quenched by dropwise addition of half-saturated aqeous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ethyl acetate as eluant. The product (+)-1-phenylpropyl acetate (0.43 g, 80%) was isolated as a colorless liquid by distillation of the solvent at reduced pressure.

Anal. for $C_{11}H_{14}O_2$, Calcd: C, 74.13; H, 7.92; found: C, 74.24; H. 8.05. $^1$H NMR (CDCl$_3$/TMS): δ 0.87 (t, 3 H, J=7), 1.79, (m, 1 H), 1.90 (m, 1 H), 2.06 (s, 3 H), 5.66 (t, 1 H, J=7), 7.1–7.7 (m, 5 H). $^{13}$C NMR (CDCl$_3$/TMS): δ 9.89, 21.23, 29.30, 77.66, 126.76, 128.81, 128.57, 140.58, 170.36. $[\alpha]_D^{25}=+103.6$, c=1.90 g/100 mL chloroform. Chiral capillary gas chromatographic analysis at 120° C. on Cyclodex B stationary phase (J & W Scientific) indicated that the enantiomeric excess of the product was 97.6%.

EXAMPLE 15

To a flask containing aminoalcohol A (0.036 g, 0.15 mmol) prepared as in Example 13 was added freshly distilled hexanal (0.30 g, 3.0 mmol) and toluene (3.0 mL). The flask was cooled to 0° C. and 1 M diethylzinc in hexane (6.0 mL) was added dropwise. After 3 hours at 0° C., acetic anhydride (1.2 mL, 13 mmol) was added. After 18 hours the mixture was diluted in ether (50 mL) and the reaction was quenched by dropwise addition of half-saturated aqeous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography 'on 220–400 mesh silica with 95% hexane and 5% ethyl acetate as eluant. The product (+)-3-octyl acetate (0.43 g, 83%) was isolated as a colorless liquid by distillation of the solvent at reduced pressure.

Anal. for $C_{10}H_{20}O_2$. Calcd: C, 69.72; H, 11.70; found: C, 69.91; H, 11.64. $^1$H NMR (CDCl$_3$/TMS): δ 0.86 (t, 6 H, J=7), 1.22–1.33 (br m, 6 H), 1.45–1.60 (m, 4 H), 2.03 (s, 3 H), 4.80 (m, 1 H). $^{13}$C NMR (CDCl$_3$/TMS): δ 9.58, 14.00, 21.25, 22.57, 25.02, 26.98, 31.62, 33.60, 75.57, 170.97. $[\alpha]_D^{25}$=+7.0, c=1.63 g/100 mL chloroform. Chiral capillary gas chromatographic analysis at 100° C. on Cyclodex B stationary phase (J & W Scientific) indicated that the enantiomeric excess of the product was 90.8%.

EXAMPLE 16

To a flask containing aminoalcohol A (0.036 g, 0.15 mmol) prepared as in Example 13 was added freshly distilled cyclohexanecarboxaldehyde (0.34 g, 3.0 mmol) and toluene (3.0 mL). The flask was cooled to 0° C. and 1 M diethylzinc in hexane (6.0 mL) was added dropwise. After 3 hours at 0° C., acetic anhydride (1.2 mL, 13 mmol) was added. After 18 hours at 25° C. the mixture was diluted in ether (50 mL) and the reaction was quenched by dropwise addition of half-saturated aqeous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ethyl acetate as eluant. The product (+)-1-cyclohexylpropyl acetate (0.54 g, 97%) was isolated as a colorless liquid by distillation at reduced pressure.

Anal. for $C_{11}H_{20}O_2$. Calcd: C, 71.70; H, 10.94; found: C, 71.48; H, 10.80. $^1$H NMR (CDCl$_3$/TMS): δ 0.85 (t, 3 H, J=7), 0.98 (m, 2 H), 1.08–1.26 (m, 3 H), 1.42–1.75 (m, 8 H), 2.04 (s, 3 H), 4.66 (m, 1 H). $^{13}$C NMR (CDCl$_3$/TMS): δ 9.80, 21.14, 24.11, 26.21, 26.58, 28.22, 40.90, 79.25, 171.09. $[\alpha]_D^{25}$=+30.1, c=1.49 g/100 mL chloroform. Chiral capillary gas chromatographic analysis at 120° C. on Cyclodex B stationary phase (J & W Scientific) indicated that the enantiomeric excess of the product was 98.5%.

EXAMPLE 17

To a vial containing aminoalcohol A (0.05 g, 0.21 mmol) prepared as in Example 13 was added a solution containing cyclopropanecarboxaldehyde (0.21 g, 3.0 mmol), toluene (3.0 mL), and 1 M diethylzinc in hexane (6.0 mL). After 3 days at room temperature, acetic anhydride (1.2 mL, 13 mmol) was added. After 2 additional days the mixture was diluted in ether (50 mL) and the reaction was quenched by dropwise addition of half-saturated aqueous ammonium chloride (50 mL). The ether layer was separated and the aqueous layer was further extracted with ether (2×50 mL). The combined ether layers were dried over magnesium sulfate whereupon the solvent was removed at reduced pressure. The residue was purified by flash chromatography on 220–400 mesh silica with 90% hexane and 10% ether as eluant. The product (+)-1-(cyclopropyl)propyl acetate (0.23 g, 54%) was isolated as a colorless liquid by distillation at reduced pressure. Anal. for $C_{11}H_{20}O_2$. Calcd: C, 71.70; H, 10.94; found: C, 71.41; H, 10.69. $^1$H NMR (CDCl$_3$/TMS): δ 0.23 (m, 1 H), 0.36 (m, 1 H), 0.43 (m, 1 H), 0.52 (m, 1 H), 1.00–1.09 (m+t, 4 H total), 1.69 (m, 2 H), 2.05 (s, 3 H), 4.20 (m, 1 H); $^{13}$C NMR (CDCl$_3$/TMS): δ 2.66, 2.82, 9.57, 14.57, 21.03, 27.45, 79.62, 170.66. $[\alpha]_D^{25}$=+26.2, c=1.04 g/100 mL chloroform. Chiral capillary gas chromatographic analysis at 55° C. on Cyclodex B stationary phase (J & W Scientific) indicated that the enantiomeric excess of the product was 96%.

EXAMPLE 18

A vial was charged with aminoalcohol A (0.0061 g, 0.025 mmol) prepared as in Example 13. To the vial was added 1.63 mL of a stock solution containing trimethylacetaldehyde (0.26 g), chlorobenzene internal standard (0.26 g), 1 M diethylzinc in hexane (6.0 mL), and toluene (3.0 mL). After 48 h acetic anhydride (0.200 mL) was added. After an additional 72 h a sample of the solution was analyzed by gas chromatography at 70° C. on a Cyclodex B stationary phase. The product 3-acetoxy-2,2-dimethylpentane was formed in 57% yield and 97% enantiomeric excess. The identity and yield of the product was established by comparison with an authentic sample prepared by treatment of racemic 2,2-dimethyl-3-pentanol with acetic anhydride.

EXAMPLE 19

A vial was charged with aminoalcohol A (0.0057 g, 0.024 mmol). To the vial was added 1.52 mL of a stock solution containing freshly distilled isobutyraldehyde (0.22 g), chlorobenzene internal standard (0.22 g), 1 M diethylzinc in hexane (6.0 mL), and toluene (3.0 mL). After 48 h acetic anhydride (0.200 mL) was added. After an additional 72 h a sample of the solution was analyzed by gas chromatography at 70° C. on a Cyclodex B stationary phase. The product 3-acetoxy-2-methylpentane was formed in 92% yield and 98% enantiomeric excess. The identity and yield of the product was established by comparison with an authentic sample prepared by treatment of racemic 2-methyl-3-pentanol with acetic anhydride.

EXAMPLE 20

A vial was charged with aminoalcohol A (0.0063 g, 0.026 mmol). To the vial was added 1.68 mL of a stock solution containing trans-2-pentenal (0.34 g), t-butylbenzene internal standard (0.25 g), 1 M diethylzinc in hexane (8.0 mL), and toluene (4.0 mL). After 48 h acetic anhydride (0.200 mL) was added. After an additional 72 h a sample of the solution was analyzed by gas chromatography at 80° C. on a Cyclodex B stationary phase. The product trans-4-hepten-3-yl acetate was formed 87% enantiomeric excess.

EXAMPLE 21

A solution of 9-borabicyclononane (0.24 g, 2.0 mmol) in THF (5 mL) was added dropwise to a solution of 5-chloro-1-pentyne (0.21 g, 2.0 mmol) in THF (5 mL). After 1 h the solvent was removed at reduced pressure. The resultant vinyl boron derivative was dissolved in toluene (5 mL) and aminoalcohol A (0.05 g, 0.21 mmol) was added. The flask was cooled to −78° C. and 1 M diethylzinc in hexane (3 mL, 3 mmol) was added via syringe. The dry ice bath was replaced with a wet ice bath and immediately a solution of isobutyraldehyde (0.17 g, 2.4 mmol) in hexane (5 mL) was added dropwise. After 1 hour the wet ice bath was removed and the mixture was stirred at room temperature for 8 h. Acetic anhydride (500 μL) was added and the mixture was allowed to stand overnight. GC analysis 130° C. on Cyclodex B revealed that trans-3-acetoxy-2-methyl-8-chlorooct-4-ene had been formed in 93% enantiomeric excess.

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specifications, as indicating the scope of the invention.

I claim:

1. A process to prepare a compound of the Formula 6:

comprising:

(a) contacting an aldehyde of formula RC(O)H with a zinc compound of formula R'ZnR" in the presence of a catalytic amount of an erythro-β-amino-alcohol of Formula 1:

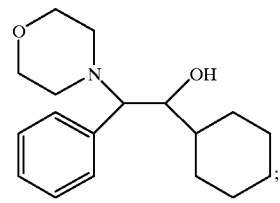

(b) further contacting the reactants with $Y_2O$ to form the corresponding ester or alcohol of Formula 6, wherein R, R', and R" are hydrocarbyl or substituted hydrocarbyl, Y is a hydrogen or alkanoyl group, and $Y_2O$ is a carboxylic acid anhydride or water.

2. The process of claim 1 wherein the erythro-β-aminoalcohol and the compound of Formula 6 are optically active.

3. The process of claim 2 wherein the compound of Formula 6 has an enantiomeric excess of greater than about 80%.

4. The process of claim 2 wherein the compound of Formula 6 has a high level of enantiomeric purity.

5. The process of claim 1 wherein Y is hydrogen or acetyl.

6. The process of claim 5 wherein:

R is selected from the group consisting of phenyl, n-hexyl, 3-thienyl, cyclohexyl, 1,1-dimethyl-3-butenyl, isopropyl, 1-butenyl, cyclopropyl, and isobutyl; and R' is selected from the group consisting of ethyl, methyl and 5-chloropentenyl.

* * * * *